United States Patent
Tsuji

(10) Patent No.: US 7,256,376 B2
(45) Date of Patent: Aug. 14, 2007

(54) MICROWAVE SENSOR AND MUTUAL INTERFERENCE PREVENTING SYSTEM BETWEEN MICROWAVE SENSORS

(75) Inventor: Masatoshi Tsuji, Otsu (JP)

(73) Assignee: Optex Co., Ltd., Shiga (JP)

( * ) Notice: Subject to any disclaimer, the term of this patent is extended or adjusted under 35 U.S.C. 154(b) by 0 days.

(21) Appl. No.: 11/092,713

(22) Filed: Mar. 30, 2005

(65) Prior Publication Data

US 2005/0236404 A1   Oct. 27, 2005

(30) Foreign Application Priority Data

Mar. 30, 2004   (JP) .............................. 2004-098745

(51) Int. Cl.
  H05B 6/64   (2006.01)
  H05B 6/50   (2006.01)
  G08B 13/18  (2006.01)
  G08B 13/00  (2006.01)

(52) U.S. Cl. ................... 219/679; 219/704; 340/567; 340/565

(58) Field of Classification Search .......... 340/567, 340/566, 565; H05B 6/64, 6/50; G08B 13/18, G08B 13/00
See application file for complete search history.

(56) References Cited

U.S. PATENT DOCUMENTS

| | | | |
|---|---|---|---|
| 4,529,972 A | | 7/1985 | Paterson et al. |
| 5,793,288 A | * | 8/1998 | Peterson et al. ............ 340/567 |
| 5,861,834 A | | 1/1999 | Sauer et al. |
| 5,986,357 A | * | 11/1999 | Myron et al. ................ 307/116 |
| 6,078,253 A | * | 6/2000 | Fowler ........................ 340/501 |
| 6,191,688 B1 | * | 2/2001 | Sprouse ...................... 340/506 |
| 6,239,736 B1 | * | 5/2001 | McDonald et al. ............ 342/28 |
| 6,331,964 B1 | * | 12/2001 | Barone ........................ 367/128 |
| 6,351,234 B1 | * | 2/2002 | Choy ............................ 342/53 |
| 6,798,341 B1 | * | 9/2004 | Eckel et al. ................. 340/521 |
| 7,081,817 B2 | * | 7/2006 | Zhevelev et al. ........... 340/567 |
| 2002/0175815 A1 | * | 11/2002 | Baldwin ..................... 340/567 |

FOREIGN PATENT DOCUMENTS

| | | |
|---|---|---|
| EP | 1 494 043 A3 | 1/2005 |
| GB | 1 390 994 | 4/1975 |
| JP | 11-39574 | 2/1999 |
| JP | 2002-311154 | 10/2002 |
| WO | 2003/107035 | 12/2003 |

\* cited by examiner

*Primary Examiner*—Daniel Robinson
(74) *Attorney, Agent, or Firm*—Wenderoth, Lind & Ponack, L.L.P.

(57) ABSTRACT

A microwave sensor is provided that transmits microwaves toward a detection area, performs an object detecting operation based on reflected waves from an object being present in the detection area, and outputs an object detection signal based on a result of the abject detecting operation, the microwave sensor being provided with a detecting operation controller for controlling the object detecting operation to be performed intermittently at a predetermined detection cycle, a time setting changer for changing time setting of the detection cycle, and a filter for preventing a signal outside of a frequency region of a signal obtained when detecting a human figure from being included in the object detection signal and from being output,

20 Claims, 6 Drawing Sheets switching
control signal S1
(first sensor)

switching
control signal S1
(second sensor)

switching control signal SO (first sensor)

switching control signal SO (second sensor)

switching control signal SO (first sensor)

switching control signal SO (second sensor)

US 7,256,376 B2

MICROWAVE SENSOR AND MUTUAL INTERFERENCE PREVENTING SYSTEM BETWEEN MICROWAVE SENSORS

CROSS-REFERENCE TO RELATED APPLICATION

The present application claims priority under 35 U.S.C. §119(a) of Patent Application Number 2004-98745, filed in Japan on Mar. 30, 2004, the subject matter of which is hereby incorporated herein by reference.

BACKGROUND OF THE INVENTION

1. Field of Invention

The present invention relates to a microwave sensor that is an active sensor using electromagnetic waves whose frequency is lower than that of visible light. In particular, the present invention relates to a microwave sensor and a mutual interference preventing system between microwave sensors in which an influence of mutual interference between their radio waves can be suppressed in the case where a plurality of microwave sensors are arranged close to each other.

2. Conventional Art

Conventionally, as one crime prevention device, microwave sensors are known in which microwaves are emitted toward a detection area, and when a human figure is present in the detection area, the human figure (intruder) is detected by receiving the reflected waves (microwaves modulated due to the Doppler effect) from the human figure.

Such a microwave sensor is provided with an antenna for emitting and receiving microwaves. Microwaves are emitted from the antenna toward a detection area, and when a human figure is present in the detection area, the reflected waves from the human figure with the frequency modulated due to the Doppler effect are received by the antenna. More specifically, in this case, the microwaves received by the antenna are modulated with respect to the frequency of the microwaves emitted from the antenna, so that the waveforms of an output signal from the microwave sensor is changed, and thus a human figure detection signal is emitted from the microwave sensor.

Generally, this type of microwave sensor is used in combination with a passive infrared sensor (PIR sensor) in which an infrared ray from a human figure in a detection area is received, and the intruder is detected based on a temperature difference between the human figure and its surroundings (see JP H11-39574A, for example). More specifically, the detection area of the microwave sensor and the detection area of the passive infrared sensor are overlapped, and the AND of their detection outputs is taken so as to supplement weaknesses of the two sensors, so that the reliability of human figure detection is enhanced.

When a plurality of such microwave sensors are arranged in the same space or one in each adjacent space, radio waves emitted from the microwave sensors may interfere each other. Normally, the antennas of microwave sensors are arranged to extend vertically in the state where sensors are installed. When a pair of the thus configured sensors are arranged, for example, on wall surfaces opposed to each other in the same room, the planes of polarization of the antennas of the microwave sensors overlap each other on the same plane, and thus their radio waves interfere with each other. Consequently, a noise is mixed in the waveforms of output signals from the microwave sensors, and thus a normal operation may be impaired. Furthermore, even when the microwave sensors are arranged one in each adjacent room, if the wall surfaces on which the microwave sensors are arranged are opposed to each other, their radio waves interfere each other in a similar manner to the above because microwaves are transmitted through walls, and thus a normal operation may be impaired.

FIG. 4 is a block diagram showing a circuit configuration of such a conventional microwave sensor 100.

As shown in FIG. 4, the microwave sensor 100 is provided with an oscillation power source 26 for oscillating microwaves, a transmitting antenna 22 for transmitting the microwaves oscillated by the oscillation power source 26 toward a detection area, a receiving antenna 21 for receiving the reflected waves of the microwaves reflected by a human figure or the like, a mixer 23 for mixing the microwaves received by the receiving antenna 21 and the voltage waveforms of the oscillation power source 26 and outputting the result, an IF amplifier 25 for amplifying the output of the mixer 23, a microprocessor 110 for controlling the entire microwave sensor 100, and an oscillation circuit 11 for supplying a clock signal CLK to the microprocessor 110. It should be noted that for the oscillation circuit 11, for example, a ceramic oscillator or a crystal oscillator can be used, but the oscillator is not limited to these.

Furthermore, a switch 24a is inserted between the mixer 23 and the IF amplifier 25, and a switch 24b is inserted between the transmitting antenna 22 and the oscillation power source 26. The switches 24a and 24b can switch an electrical connection state in response to an external signal, and are connected so as to be switchable in synchronization.

The microprocessor 110 has a switching control portion 10a for outputting a switching control signal S0 that controls switching of the switches 24a and 24b, a timer 10b for determining the cycle of the switching control signal S0 that is output from the switching control portion 10a, and a time setting portion 10c for setting a detection cycle (for example, 250 μs) for the timer 10b. For the ON time of the switching control signal S0 in each cycle, a necessary time can be ensured by using, for example, another timer (not shown) or a software timer.

The microprocessor 110 generates a system clock by dividing the clock signal CLK supplied from the oscillation circuit 11, and operates each portion of the microprocessor 110 based on the system clock. Since the timer 10b also operates based on the system clock, the accuracy of time of the timer 10b depends on the accuracy of the system clock or the clock signal CLK of, the oscillation circuit 11 from which the system clock is generated.

When the switching control signal S0 that is output from the switching control portion 10a is ON, both of the switches 24a and 24b are switched to be electrically connected, and thus the microwave sensor 100 performs an operation of detecting a human figure or the like. More specifically, microwaves are transmitted from the transmitting antenna 22 toward a detection area, and when a human figure or the like is present in the detection area, the reflected waves from the human figure with the frequency modulated due to the Doppler effect are received by the receiving antenna 21. The received reflected waves are mixed with the voltage waveforms of the oscillation power source 26 by the mixer 23 and amplified by the IF amplifier 25, and then an IF output signal IFout0 from the IF amplifier 25 is obtained as a human figure detection signal output from the microwave sensor 100. When there is no human figure or the like in the detection area, reflected waves whose frequency is modulated are not received by the receiving antenna 21. Therefore, the IF frequency of the IF output signal IFout0 from the IF amplifier 25 is "0," and thus a human Figure detection signal is not output from the microwave sensor 100.

On the other hand, when the switching control signal S0 that is output from the switching control portion 10a is OFF, both of the switches 24a and 24b are switched to be electrically disconnected, and thus the microwave sensor 100 does not perform an operation of detecting a human figure or the like.

FIGS. 5(a) and 5(b) are examples of a time chart for comparing switching control signals S0 when two conventional microwave sensors 100 are used. FIG. 5(a) shows the switching control signal S0 of a first microwave sensor, and FIG. 5(b) shows the switching control signal S0 of a second microwave sensor.

As shown in FIGS. 5(a) and 5(b), these microwave sensors 100 perform operations of detecting a human figure or the like intermittently at a predetermined detection cycle. The first microwave sensor 100 has a cycle T01a, and performs a detection operation during a time T02a during which the switching control signal S0 is ON, in each cycle. The second microwave sensor 100 has a cycle T01b, and performs a detection operation during a time T02b during which the switching control signal S0 is ON, in each cycle. The cycle of the switching control signal S0 may be set to, for example, 250 μs, and the ON time may be set to, for example, 50 μs, but the time setting is not limited to this.

When the two microwave sensors 100 are used close to each other, for example, if the timings at which the switching control signals S0 of the first microwave sensor and the second microwave sensor are ON are sufficiently apart from each other on the time axis, it can be said that their radio waves do not interfere with each other and thus a normal operation is not impaired.

Furthermore, when the cycle T01a and the cycle T01b of the switching control signals S0 of the microwave sensors 100 are completely identical to each other, the timings at which the switching control signals S0 are ON are always kept at the same distance on the time axis from each other. Therefore, unless the timings at which the switching control signals S0 are ON overlap each other accidentally from the beginning, their radio waves do not interfere with each other.

FIGS. 6(a) and 6(b) are examples of a time chart for comparing switching control signals S0 at a different time point from that of FIGS. 5(a) and 5(b), when two conventional microwave sensors 100 are used in a similar manner. FIG. 6(a) shows the switching control signal S0 of a first microwave sensor, and FIG. 6(b) shows the switching control signal S0 of a second microwave sensor. FIG. 7 is an example of a waveform of an IF output signal IFout0 from the IF amplifier 25 of one of the microwave sensors 100 in this case.

As described above, the cycles of the switching control signals S0 are determined by the timers 10b of the microprocessors 110, and the accuracy of time of the timers 10b depends on the accuracy of the system clocks or the clock signals CLK of the oscillation circuits 11 from which the system clocks are generated. Although the accuracy of frequency of, for example, a ceramic oscillator or a crystal oscillator used for the oscillation circuits 11 is high, there is a slight error with respect to a reference frequency, and this error is different from oscillator to oscillator. More specifically, the cycles of the switching control signals S0 are slightly different for each microwave sensor 100 in the strict sense, and the cycle T01a and the cycle T01b of the switching control signals S0 in FIGS. 6(a) and 6(b) are slightly different from each other.

Therefore, a distance on the time axis between the timings at which the switching control signals S0 of the first microwave sensor and the second microwave sensor are ON changes in a long period of time, and the timings at which the switching control signals S0 are ON almost overlap each other in the course of time as shown in FIGS. 6(a) and 6(b). In this state, their radio waves interfere each other, and thus a noise is generated. This state continues for a while, and after a further time has passed, the timings at which the switching control signals S0 are ON do not overlap each other again, and then the same process is repeated cyclically. When the noise caused by such interference between radio waves is referred to as "interference noise," the interference noise in the IF output signal IFout0 from the IF amplifier 25 of one of the microwave sensors 100 has a waveform, for example, as shown in FIG. 7. In this example, the frequency of the interference noise is about 14 Hz.

Since the interference noise is generated in a certain cycle based on the cycle T01a and the cycle T01b of the switching control signals S0, it is possible to calculate the cycle of the interference noise or a frequency f0 of the interference noise, which is an inverse number of the cycle. When the ratio of a difference between the frequencies of the clock signals CLK of the oscillation circuits 11 of the two microwave sensors 100 is taken as "A," and the cycle of the switching signals S0 is taken as "T01," the frequency f0 of the interference noise can be expressed by the following equation.

$$f0 = A/T01 \qquad (1)$$

When A=3530 [ppm] and T01=250 [μs] are inserted into Equation 1, f0≈14.1 [Hz] results, which is nearly equal to the frequency of the interference noise shown in FIG. 7.

It should be noted that the ratio "A" of a difference between the frequencies of the clock signals CLK actually can take a value in a range up to about several thousands ppm in the case of, for example, a ceramic oscillator, and takes a different value from oscillator to oscillator. Therefore, the frequency of an interference noise differs based on the combination of two microwave sensors 100.

In the case where the frequency of the interference noise is within the frequency band (for example, 5 to 50 Hz) of a signal that is output when the microwave sensor 100 detects a human figure or the like, the interference noise is amplified by the IF amplifier 25, and is output as a human figure detection signal from the microwave sensor 100.

As one of means for preventing such interference between radio waves, the frequencies of microwaves emitted by microwave sensors are differentiated from each other.

Furthermore, there is also a method in which microwave sensors are electrically connected to each other to use a common synchronizing signal, so that timings of detection operations performed by the microwave sensors do not overlap each other.

Alternatively, microwave sensors have been proposed in which the antennas of the microwave sensors are arranged to be inclined with respect to the vertical direction, so that the planes of polarization of the antennas do not overlap each other on the same plane to prevent the interference (see JP 2002-311154A, for example). The microwave sensors provided with an antenna for emitting microwaves toward a detection area and for receiving the microwaves reflected from the detection area, in which a human figure in the detection area is detected based on the microwaves received by the antenna, is characterized in that the antenna is provided to extend in an oblique direction, not in the vertical direction or the horizontal direction in the state where sensors are installed.

However, when the frequencies of the microwaves emitted by the microwave sensors are differentiated from each other as the above-described conventional technique, there is the problem of the frequency band that can be actually used being often regulated by, for example, national laws and systems. Therefore, a large number of microwave sensors using different frequencies cannot be prepared.

Furthermore, when microwave sensors are electrically connected to each other to use a common synchronizing signal, a wiring work becomes necessary. Thus, not only is the installation work difficult, but also new problems stemming from the wiring may occur (for example, a normal operation of a part of or all microwave sensors is impaired due to contact failure of wires, disconnection of wires or the like).

The method for arranging the antennas of microwave sensors to be inclined with respect to the vertical direction may be difficult to adapt in practice in some installation locations.

SUMMARY OF THE INVENTION

In view of these issues of conventional techniques, an object of the present invention is to provide a microwave sensor in which an influence of mutual interference between the radio waves is suppressed with a simple structure so as to ensure a high reliability even when a plurality of microwave sensors are arranged close to each other, in which there is no particular limitation regarding the installation location, and in which the installation is easy, and a mutual interference preventing system between such microwave sensors.

In order to achieve the above-described object, the microwave sensor of the present invention transmits microwaves toward a detection area, performs an object detecting operation based on reflected waves from an object being present in the detection area, and outputs an object detection signal based on the result of the object detecting operation, the microwave sensor comprising a detecting operation controller for controlling the object detecting operation to be performed intermittently at a predetermined detection cycle, a time setting changer for changing time setting of the detection cycle, and a filter for preventing a signal outside of a frequency region of a signal obtained when detecting a human figure from being included in the object detection signal and being output.

Herein, for the detection cycle, a time setting of, for example, about 250 μs can be used, but the time setting is not limited to this. Furthermore, when the time setting is changed, for example, 260 μs can be used by adding 10 μs, but the change is not limited to this. When the plurality of microwave sensors are used, the time setting is changed in this manner for each of the microwave sensors so that their detection cycles are different from each other.

According to the microwave sensor of the present invention, when the plurality of microwave sensors are used close to each other, the frequency of an interference noise that is generated by mutual interference between their radio waves can be a high frequency that is outside of a frequency region of a signal output when detecting a human figure or the like. The filter prevents the interference noise with such a high frequency from being included in the object detection signal and being output, and thus almost only the original signal obtained when detecting a human figure or the like is output in the object detection signal. Thus, it is possible to suppress an influence of mutual interference between their radio waves of the microwave sensors, and thus a high reliability of human figure detection is ensured. Furthermore, it is not necessary to wire between the microwave sensors or to arrange antennas or the like to be inclined, and thus there is no particular limitation regarding the installation location of the microwave sensors and the installation is easy. The frequency of the microwaves that are used is only one common frequency, and thus regulations by, for example, national laws and systems do not become a problem at all.

Furthermore, the microwave sensor according to the present invention may comprise an information input device for inputting information relating to time setting of the detection cycle, in which the time setting changer changes time setting of the detection cycle based on information input by the information input device.

Herein, for the information input device, for example, at least one DIP switch or at least one jumper switch can be used, but the information input device is not limited to these.

According to the microwave sensor of the present invention, when information relating to time setting of the detection cycle is input by the information input device, the time setting of the detection cycle is changed based on the input information. Thus, it is possible to change a detection cycle by operating the information input device to change input information. If the information input devices are easy to operate, when, for example, the plurality of microwave sensors are installed, it is possible to suppress an influence of mutual interference between their radio waves by setting in such a manner that the detection cycles of the microwave sensors are different from each other. Thus, it is not necessary to prepare a large number of kinds of microwave sensors whose detection cycles are differentiated from each other by changing information input by the information input devices at the time of production or to use them in different manners at the time of installation, so that the cost for production and sales management can be reduced.

Furthermore, the microwave sensor according to the present invention may further comprise a passive infrared sensor that receives an infrared ray from the detection area, and detects an intruding object based on a temperature difference from its surroundings, in which the object detection signal is allowed to be output only when the passive infrared sensor detects an intruding object.

According to the microwave sensor of the present invention, even when a part of an interference noise passes through the filter by a low level, the object detection signal is not output unless the passive infrared sensor detects an intruding object. Thus, the reliability of human figure detection is further enhanced.

Furthermore, the mutual interference preventing system between the microwave sensors of the present invention by which when the plurality of microwave sensors according to any one of the above are used close to each other, mutual interference between the microwave sensors is prevented, is such that the detection cycles are differentiated from each other by at least a predetermined value by the time setting changers of the microwave sensors.

Herein, when a lower limit of a frequency of an acceptable noise that is determined based on an upper limit of a frequency region of a signal obtained when detecting a human figure and characteristics of the filter is taken as fLow, when a longest one of the detection cycles of the microwave sensors is taken as Tmax, and when a difference in detection cycle between any two microwave sensors combined is taken as ΔT, $$\Delta T \geq f\text{Low} \times T\text{max}^2$$

is satisfied. When a frequency region of a signal obtained when detecting a human figure is, for example, 5 to 50 Hz, in order to attenuate the interference noise by 24 dB or more by using a quartic filter (cutoff frequency=50 Hz) as the low-pass filter, it is sufficient that fLow=100 [Hz] is inserted to determine the detection cycle for each of the microwave sensors.

According to the mutual interference preventing system between the microwave sensors of the present invention, when the plurality of microwave sensors are used close to each other, it is possible to suppress an interference noise that is generated by mutual interference between their radio waves from being included in the object detection signal and being output, and thus almost only the original signal obtained when a human figure or the like is detected is output in the object detection signal. Thus, it is possible to prevent an influence of mutual interference between their radio waves of the microwave sensors, and thus a high reliability of human figure detection is ensured.

DESCRIPTION OF THE PREFERRED EMBODIMENTS

Hereinafter, embodiments of the present invention will be described with reference to the drawings.

Structure of a Microwave Sensor

Figure 1:
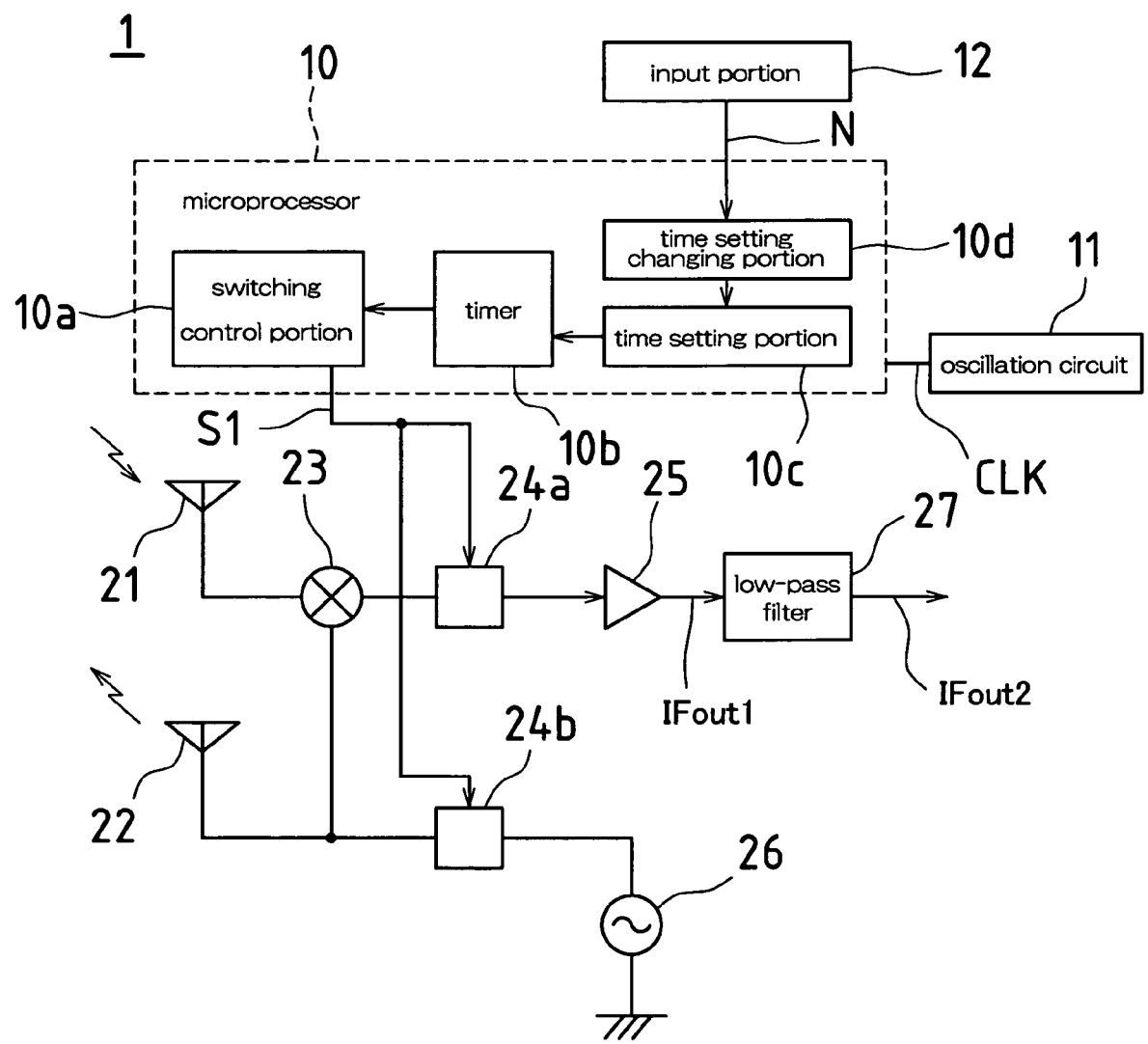
FIG. 1 is a block diagram showing a circuit configuration of a microwave sensor associated with one embodiment of the present invention.
Figure 4:
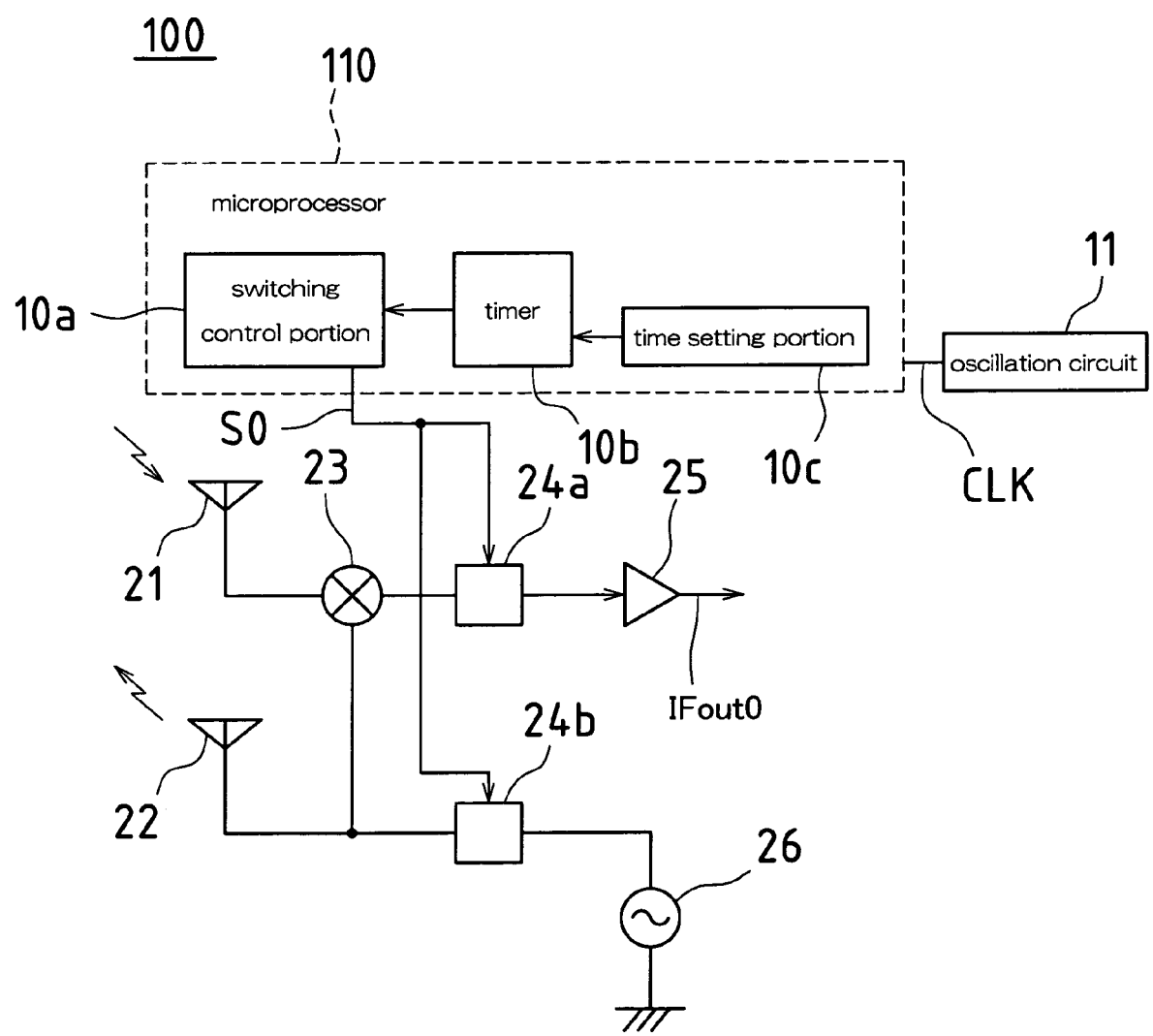
FIG. 4 is a block diagram showing a circuit configuration of a conventional microwave sensor.
Figure 5A:
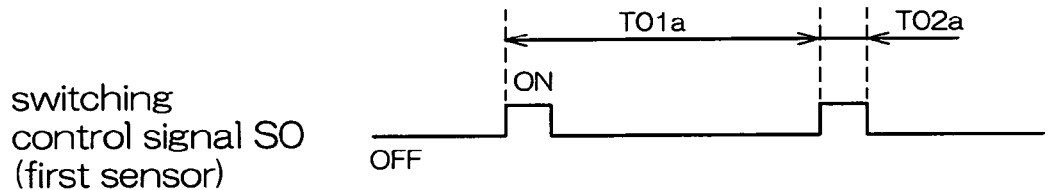
FIG. 5(a) is an example of a time chart for comparing switching control signals when two conventional microwave sensors are used, and shows the switching control signal of a first microwave sensor.
Figure 5B:
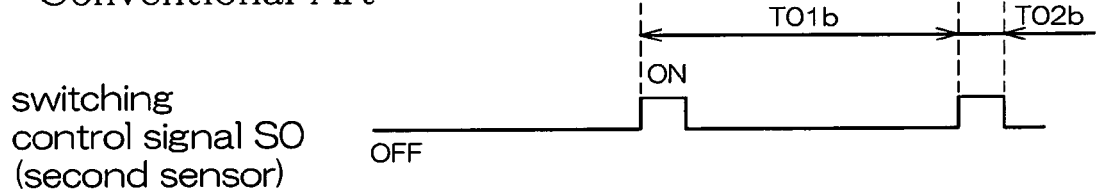
FIG. 5(b) is an example of a time chart for comparing switching control signals when two conventional microwave sensors are used, and shows the switching control signal of a second microwave sensor.
Figure 6A:
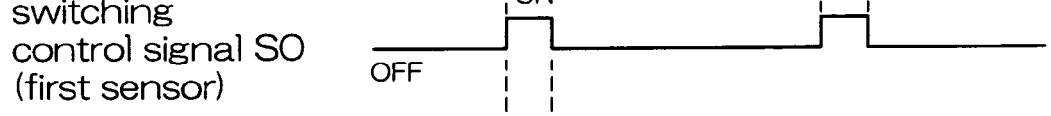
FIG. 6(a) is an example of a time chart for comparing switching control signals at a different time point from that of FIG. 5 when two conventional microwave sensors are used, and shows the switching control signal of a first microwave sensor.
Figure 6B:
FIG. 6(b) is an example of a time chart for comparing switching control signals at a different time point from that of FIG. 5 when two conventional microwave sensors are used, and shows the switching control signal of a second microwave sensor.
Figure 7:
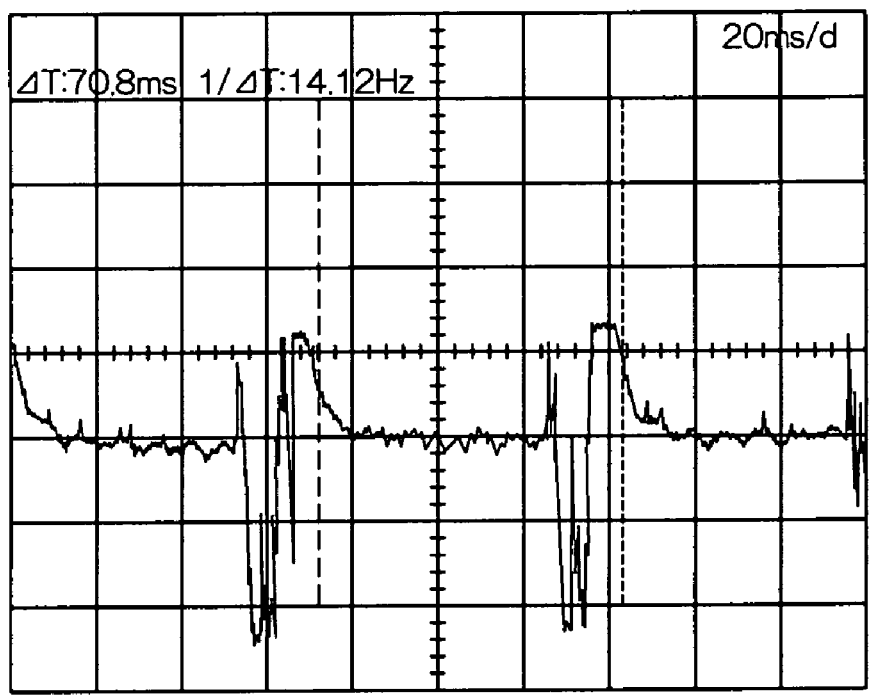
FIG. 7 is an example of an output waveform from an IF amplifier of one of the microwave sensors in FIG. 6.

FIG. 1 is a block diagram showing a circuit configuration of a microwave sensor 1 associated with one embodiment of the present invention. The same components as in the conventional example described with reference to FIG. 4 bear the same reference numbers.

As shown in FIG. 1, the microwave sensor 1 is provided with an oscillation power source 26 for oscillating microwaves, a transmitting antenna 22 for transmitting the microwaves oscillated by the oscillation power source 26 toward a detection area, a receiving antenna 21 for receiving the reflected waves of the microwaves reflected by an object such as a human figure, a mixer 23 for mixing the microwaves received by the receiving antenna 21 and the voltage waveforms of the oscillation power source 26 and outputting the result, an IF amplifier 25 for amplifying the output of the mixer 23, a low-pass filter 27 for preventing the output from the IF amplifier 25 except for signals in the frequency band obtained when a human figure or the like is detected from passing through, a microprocessor 10 for controlling the entire microwave sensor 1, an oscillation circuit 11 for supplying a clock signal CLK to the microprocessor 10, and an input portion 12 for inputting information to the microprocessor 10.

Herein, for the oscillation circuit 11, for example, a ceramic oscillator or a crystal oscillator can be used, but the oscillation circuit is not limited to these. For the input portion 12, for example, at least one DIP switch with a plurality of built-in switches can be used, but the input portion is not limited to this, and for example, at least one jumper switch can be also used.

Furthermore, a switch 24a is inserted between the mixer 23 and the IF amplifier 25, and a switch 24b is inserted between the transmitting antenna 22 and the oscillation power source 26. The switches 24a and 24b can switch an electrical connection state in response to an external signal, and are connected so as to be switchable in synchronization.

The microprocessor 10 has a switching control portion 10a for outputting a switching control signal S1 that controls switching of the switches 24a and 24b, a timer 10b for determining the cycle of the switching control signal S1 that is output from the switching control portion 10a, a time setting portion 10c for setting a time set value (for example, 250 µs) corresponding to a detection cycle T11 for the timer 10b, and a time setting changing portion 10d for changing the time set value set by the time setting portion 10c, based on information that is input from the input portion 12. Herein, information that is input from the input portion 12 is an integer N within a range of 0 to 5, and the time setting changing portion 10d adds an add time ΔT that is determined by the following equation to the time set value that is set by the time setting portion 10c.

$$\Delta T = 10 \times N \ [\mu s] \quad (2)$$

If an original time set value is 250 µs, 10 µs is added as the add time ΔT when N=1, and 260 µs is set as the detection cycle T11 for the timer 10b. It should be noted that the add time ΔT is determined so as not to exceed an ON time T12 (for example, 50 µs) of the switching control signal S1 in each cycle, even at a maximum. For the ON time T12 of the switching control signal S1, a necessary time can be ensured by using, for example, another timer (not shown) or a software timer of the microprocessor 10.

When the switching control signal S1 that is output from the switching control portion 10a is ON, both of the switches 24a and 24b are switched to be electrically connected, and thus the microwave sensor 1 performs an operation of detecting a human figure or the like. More specifically, microwaves are transmitted from the transmitting antenna 22 toward a detection area, and when a human figure or the like is present in the detection area, the reflected waves from the human figure with the frequency modulated due to the Doppler effect are received by the receiving antenna 21. The received reflected waves are mixed with the voltage waveforms of the oscillation power source 26 by the mixer 23, and amplified by the IF amplifier 25. Among an IF output signal IFout1 from the IF amplifier 25, an IF output signal IFout2 that has passed through the low-pass filter 27 is obtained as a human figure detection signal output from the microwave sensor 1. When there is no human figure or the like in the detection area, reflected waves whose frequency is modulated are not received by the receiving antenna 21. Therefore, the IF frequency of the IF output signal IFout2, which is obtained after the IF output signal IFout1 from the IF amplifier 25 passes through the low-pass filter 27, is "0," and thus a human figure detection signal is not output from the microwave sensor 1.

On the other hand, when the switching control signal S1 that is output from the switching control portion 10a is OFF, both of the switches 24a and 24b are switched to be electrically disconnected, and thus the microwave sensor 1 does not perform an operation of detecting a human figure or the like.

Example of a case where two microwave sensors are used

Figure 2:
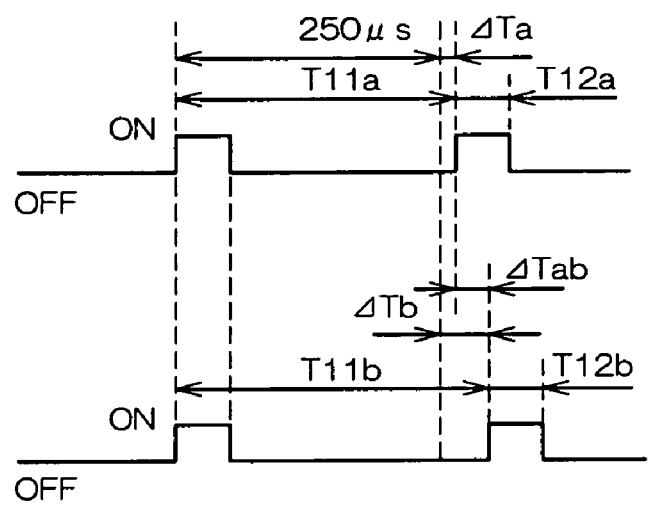
FIG. 2(a) is an example of a time chart for comparing switching control signals when two microwave sensors associated with one embodiment of the present invention are used, and shows the switching control signal of a first microwave sensor.
FIG. 2(b) is an example of a time chart for comparing switching control signals when two microwave sensors associated with one embodiment of the present invention are used, and shows the switching control signal of a second microwave sensor.
Figure 3:
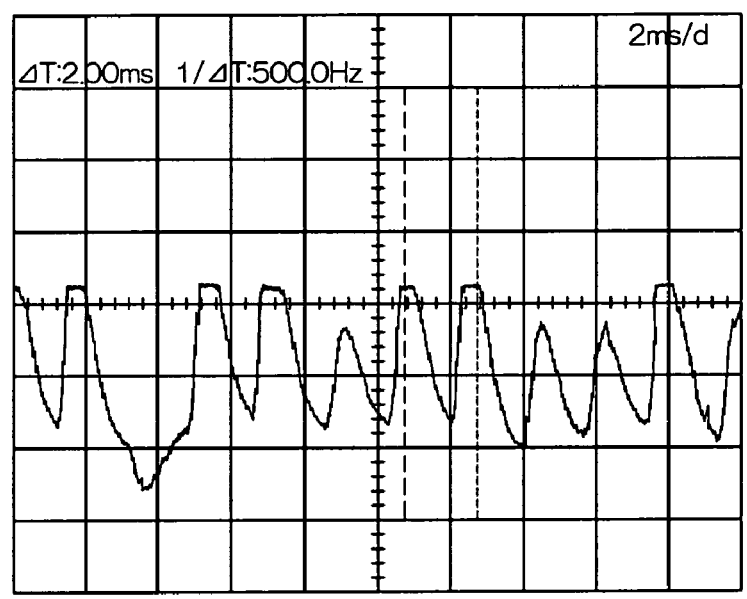
FIG. 3(a) is an example of an output waveform from an IF amplifier of one of the microwave sensors in FIG. 2, and shows an IF output signal before passing through a low-pass filter.
FIG. 3(b) is an example of an output waveform from an IF amplifier of one of the microwave sensors in FIG. 2, and shows an IF output signal after passing through a low-pass filter.
Figure 3:
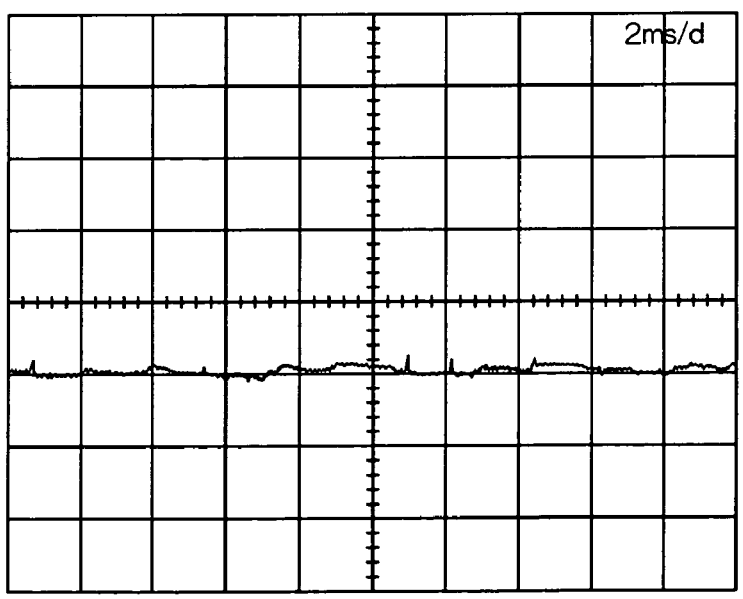

FIGS. 2(a) and 2(b) are examples of a time chart for comparing switching control signals S1 when two microwave sensors 1 associated with one embodiment of the present invention are used. FIG. 2(a) shows the switching control signal S1 of a first microwave sensor, and FIG. 2(b) shows the switching control signal S1 of a second microwave sensor. FIGS. 3(a) and 3(b) are examples of an output waveform from the IF amplifier 25 of one of the microwave sensors 1 in this case. FIG. 3(a) shows an IF output signal IFout1 before passing through the low-pass filter 27, and FIG. 3(b) shows an IF output signal IFout2 after passing through the low-pass filter 27.

As shown in FIGS. 2(a) and 2(b), these microwave sensors 1 perform operations of detecting a human figure or the like intermittently at a predetermined detection cycle. In the first microwave sensor 1, information that is input from the input portion 12 to the microprocessor 10 is N=1, the add time $\Delta Ta=10$ [μs], and the detection cycle $T11a=260$ [μs]. In the second microwave sensor 1, information that is input from the input portion 12 to the microprocessor 10 is N=4, the add time $\Delta Tb=40$ [μs], and the detection cycle $T11b=290$ [μs]. However, the time setting is not limited to this.

As described in the explanation of the conventional technique, when two microwave sensors 1 are used close to each other, the timings at which the switching control signals S1 of the first and the second microwave sensors are ON overlap each other in the course of time, and thus an interference noise is generated. Since the interference noise is generated in a certain cycle based on the cycle T11a and the cycle T11b of the switching control signals S1, it is possible to calculate the cycle of the interference noise or a frequency f of the interference noise, which is an inverse number of the cycle. When a difference between the cycle T11a and the cycle T11b is taken as $\Delta Tab$, and the cycle of one of the switching control signals S1 is taken as T11, the frequency f of the interference noise can be expressed by the following equation.

$$f = \Delta Tab / T11^2 \quad (3)$$

When $\Delta Tab = 290 \cdot 260 = 30$ [μs] and $T11 = 260$ [μs] are inserted into Equation 3, $f \approx 444$ [Hz] results, and thus a value close to the frequency (about 500 Hz) of the interference noise shown in FIG. 3(a) is obtained.

Furthermore, Equation 3 shows that even when there is a slight difference between the frequencies of the clock signals CLK of the oscillation circuits 11 of the two microwave sensors 1, the value of $\Delta Tab$ is changed only slightly in accordance with the difference, and the calculated value itself of the frequency f of the interference noise is not changed significantly. For example, when the difference between the frequencies of the clock signals CLK is 2000 ppm in a similar case to the above, $\Delta Tab$ is changed by ±0.52 μs, but the frequency f of the interference noise is only about 436 Hz or about 451 Hz. Even when the difference between the frequencies of the clock signals CLK is 4000 ppm, which is twice as large as the above, and $\Delta Tab$ is changed by ±1.04 μs, the frequency f of the interference noise is only about 428 Hz or about 459 Hz. This is a significant difference from the case of Equation 1 in the conventional technique in which when the difference between the frequencies of the clock signals CLK is doubled, the frequency f0 of the interference noise is accordingly doubled.

Furthermore, as seen from Equation 3, the frequency f of the interference noise depends on the difference $\Delta Tab$ between the cycles of the switching control signals S1 and the detection cycle T11. Therefore, when $\Delta Tab$ is determined in an appropriate range in accordance with the detection cycle T11 in such a manner that the frequency f of the interference noise is larger than the frequency band (for example, 5 to 50 Hz) of a signal output when a human figure or the like is detected, and they are sufficiently apart from each other on the frequency axis, the interference noise can be attenuated to a sufficiently low level by the low-pass filter 27.

For example, in order to attenuate the interference noise by 24 dB or more by using a quartic low-pass filter (cutoff frequency=50 Hz) as the low-pass filter 27, it is sufficient that the lower limit of the frequency f of the interference noise is 100 Hz. The frequency f of the interference noise becomes 100 Hz or more, when the following condition formula is satisfied.

$$\Delta Tab \geq 100 \times T11^2 \quad (4)$$

When the value (260 μs) of the detection cycle T11a of the first microwave sensor 1 is inserted into T11 of Conditional Formula 4, the following formula is obtained.

$$\Delta Tab \geq 6.76 [\mu s] \quad (5)$$

When the value (290 μs) of the detection cycle T11b of the second microwave sensor 1 is inserted into T11 of the Conditional Formula 4, the following formula is obtained.

$$\Delta Tab \geq 8.41 [\mu s] \quad (6)$$

Thus, in order to satisfy both Conditional Formulas 5 and 6, it is sufficient that Conditional Formula 6 corresponding to the longer detection cycle is satisfied, that is, $\Delta Tab$ is 8.41 μs or more.

If the smallest setting unit of the timer 10b in the microprocessor 10 of the microwave sensor 1 is, for example, 1 μs, it is sufficient that $\Delta Tab$ is set to be always 9 μs or more by rounding up numerical digits after the decimal point. In the explanation with reference to FIG. 1, the example has been described in which when information input from the input portion 12 is an integer N within a range of 0 to 5, the add time ΔT determined by Equation 2 is added to the time set value set by the time setting portion 10c, but, for example, the following equation can be used alternatively in the view of the above result.

$$\Delta T = 9 \times N \ [\mu s] \tag{7}$$

Thus, if the numerical values N, which is information input from the input portion 12 to the microprocessor 10 of each of the microwave sensors 1, are differentiated from each other, it is possible to set a difference that is at least 9 µs between the detection cycles. For the input portions 12, for example, rotary DIP switches can be used in which the position numbers of the DIP switch are configured so as to directly correspond to the numerical values N. In this case, the frequency f of the interference noise can be kept apart sufficiently from the frequency band of a signal output when a human figure or the like is detected only by a simple operation of differentiating the position numbers of the DIP switches of the microwave sensors 1 from each other. However, the configuration of the input portions 12 is not limited to this.

As described above, when two microwave sensors 1 are used, if information input from the input portion 12 to the microprocessor 10 is different from the other so that the difference between the detection cycles is at least the predetermined value that is determined as in the above explanation, the IF output signal IFout2 after passing through the low-pass filter 27 has a waveform, for example, as shown in FIG. 3(b). Since the interference noise has been eliminated almost completely, an influence of mutual interference between their radio waves is suppressed so as to ensure a high reliability of the microwave sensors 1.

Example of a Case Where Three or More Microwave Sensors are Used

In the above explanation, the case where two microwave sensors 1 are used close to each other has been described, but the present invention also can be applied to the case where three or more microwave sensors are used. More specifically, information input from the input portion 12 to the microprocessor 10 is differentiated for each of the microwave sensors 1 so that a difference between the detection cycles is always not less than a predetermined value in any combination of the microwave sensors 1, and thus an influence of mutual interference of their radio waves is suppressed.

As a method for utilizing the input portions 12 of the microwave sensors 1, it is possible to prepare a plurality of kinds of input portions with different input information settings in advance at the time of production in, for example, a plant, and to display the contents of the input information settings on, for example, a part of an outer cover or a product package of the microwave sensors 1 for identification. Thus, when a plurality of microwave sensors 1 are installed close to each other, the installation can be performed while confirming the contents of the input information settings to choose a combination in which mutual interference does not occur.

Alternatively, when the input portions 12 are realized by DIP switches and the covers of the microwave sensors 1 can be opened at, for example, the time of installation so as to manually change the settings of the DIP switches, it is sufficient that the settings or the position numbers of the DIP switches are different from each other. All of the input information settings at the time of production can be identical to each other, and it is not necessary to display the contents of the input information settings.

According to the embodiment, even when a plurality of microwave processors 1 are used close to each other, it is possible to suppress an influence of mutual interference of their radio waves so as to ensure a high reliability only by changing the settings of the detection cycle of the switching control signal S1 for each of the microwave sensors 1. As the frequencies of the microwaves used by the microwave sensors 1, only common frequency is sufficient, and thus regulations by, for example, national laws and systems do not become a problem at all. It is not necessary to wire between the microwave sensors 1, or to arrange antennas or the like to be inclined, and thus the installation work is very easy.

Other Usage Examples and Modified Examples

Furthermore, the microwave sensor 1 can be further provided with a passive infrared sensor in which an infrared ray from a human figure in a detection area is received, and the intruder is detected based on a temperature difference between the human figure and its surroundings, and the AND of the detection outputs of the sensors can be regarded as an output indicating detection of a human figure (a human figure detection signal is allowed to be output from the microwave sensor 1 only when the passive infrared sensor detects a human figure) so that the reliability of human figure detection is enhanced. It should be noted that the detection area of the microwave sensor 1 and the detection area of the passive infrared sensor do not always overlap each other in the strict sense, but it is desirable that the main portions of these detection areas overlap each other to the extent possible.

The invention may be embodied in other forms without departing from the spirit or essential characteristics thereof. The embodiment disclosed in this application is to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A microwave sensor for transmitting microwaves toward a detection area, performing an object detecting operation based on reflected waves from an object being present in the detection area, and outputting an object detection signal based on a result of the object detecting operation, the microwave sensor comprising:
   a detecting operation controller for controlling the object detecting operation to be performed intermittently at a predetermined detection cycle,
   a time setting changer for changing a time setting of the detection cycle, and
   an electrical filter for preventing an electrical signal outside of a frequency region of an electrical signal obtained when detecting a human figure from being output in the object detection signal.

2. The microwave sensor according to claim 1, further comprising:
   an information input device for inputting information relating to the time setting of the detection cycle,
   wherein the time setting changer changes time setting of the detection cycle based on information input by the information input device.

3. The microwave sensor according to claim 2, wherein the information input device is at least one DIP switch.

4. The microwave sensor according to claim 2,
wherein the information input device is at least one jumper switch.

5. The microwave sensor according to claim 1, further comprising:
a passive infrared sensor for receiving an infrared ray from the detection area, and for detecting an intruding object based on a temperature difference from its surroundings,
wherein the object detection signal is allowed to be output only when the passive infrared sensor detects an intruding object.

6. A mutual interference preventing system for preventing mutual interference between a plurality of microwave sensors that are used close to each other,
wherein each of the plurality of microwave sensors is a microwave sensor according to claim 1, and
wherein the detection cycles are differentiated from each other by at least a predetermined value by the time setting changers of the microwave sensors.

7. The mutual interference preventing system according to claim 6, wherein
when a lower limit of a frequency of an acceptable noise that is determined based on an upper limit of a frequency region of a signal obtained when detecting a human figure and characteristics of the filter is taken as fLow,
when a longest one of the detection cycles of the microwave sensors is taken as Tmax, and
when a difference in detection cycle between any two microwave sensors combines is taken as $\Delta T$,
$\Delta T \geq fLow \times Tmax^{22}$ is satisfied.

8. A mutual interference preventing system for preventing mutual interference between a plurality of microwave sensors that are used close to each other,
wherein each of the plurality of microwave sensors is a microwave sensor according to claim 5, and
wherein the detection cycles are differentiated from each other by at least a predetermined value by the time setting changers of the microwave sensors.

9. The mutual interference preventing system according to claim 8, wherein
when a lower limit of a frequency of an acceptable noise that is determined based on an upper limit of a frequency region of a signal obtained when detecting a human figure and characteristics of the filter is taken as fLow,
when a longest one of the detection cycles of the microwave sensors is taken as Tmax, and
when a difference in detection cycle between any two microwave sensors combined is taken as $\Delta T$,
$\Delta T \geq fLow \times Tmax^2$ is satisfied.

10. The microwave sensor according to claim 2, further comprising:
a passive infrared sensor for receiving an infrared ray from the detection area, and for detecting an intruding object based on a temperature difference from its surroundings,
wherein the object detection signal is allowed to be output only when the passive infrared sensor detects an intruding object.

11. The microwave sensor according to claim 3, further comprising:
a passive infrared sensor for receiving an infrared ray from the detection area, and for detecting an intruding object based on a temperature difference from its surroundings,
wherein the abject detection signal is allowed to be output only when the passive infrared sensor detects an intruding object.

12. The microwave sensor according to claim 4, further comprising:
a passive infrared sensor for receiving an infrared ray from the detection area, and for detecting an intruding object based on a temperature difference from its surroundings,
wherein the object detection signal is allowed to be output only when the passive infrared sensor detects an intruding object.

13. A mutual interference preventing system for preventing mutual interference between a plurality of microwave sensors that are used close to each other,
wherein each of the plurality of microwave sensors is a microwave sensor according to claim 2, and
wherein the detection cycles are differentiated from each other by at least a predetermined value by the time setting changers of the microwave sensors.

14. A mutual interference preventing system for preventing mutual interference between a plurality of microwave sensors that are used close to each other,
wherein each of the plurality of microwave sensors is a microwave sensor according to claim 3, and
wherein the detection cycles are differentiated from each other by at least a predetermined value by the time setting changers of the microwave sensors.

15. A mutual interference preventing system for preventing mutual interference between a plurality of microwave sensors that are used close to each other,
wherein each of the plurality of microwave sensors is a microwave sensor according to claim 4, and
wherein the detection cycles are differentiated from each other by at least a predetermined value by the time setting changers of the microwave sensors.

16. The mutual interference preventing system according to claim 13, wherein
when a lower limit of frequency of an acceptable noise that is determined based on an upper limit of a frequency region of a signal obtained when detecting a human figure and characteristics of the filter is taken as fLow,
when a longest one of the detection cycles of the microwave sensors is taken as Tmax, and
when the difference in detection cycle between any two microwave sensors combined is taken as $\Delta T$,
$\Delta T \geq fLow \times Tmax^2$ is satisfied.

17. The mutual interference preventing system according to claim 14, wherein
when a lower limit of frequency of an acceptable noise that is determined based on an upper limit of a frequency region of a signal obtained when detecting a human figure and characteristics of the filter is taken as fLow,
when a longest one of the detection cycles of the microwave sensors is taken as Tmax, and
when the difference in detection cycle between any two microwave sensors combined is taken as $\Delta T$,
$\Delta T \geq fLow \times Tmax^2$ is satisfied.

18. The mutual interference preventing system according to claim 15, wherein
when a lower limit of frequency of an acceptable noise that is determined based on an upper limit of a frequency region of a signal obtained when detecting a human figure and characteristics of the filter is taken as fLow, when a longest one of the detection cycles of the microwave sensors is taken as Tmax, and when the difference in detection cycle between any two microwave sensors combined is taken as $\Delta T$, $\Delta T \geq fLow \times Tmax^2$ is satisfied.

19. A mutual interference preventing system for preventing mutual interference between a plurality of microwave sensors that are used close to each other, wherein each of the plurality of microwave sensors is a microwave sensor according to claim 10, and wherein the detection cycles are differentiated from each other by at least a predetermined value by the time setting changers of the microwave sensors.

20. A mutual interference preventing system for preventing mutual interference between a plurality of microwave sensors that are used close to each other, wherein each of the plurality of microwave sensors is a microwave sensor according to claim 11, and wherein the detection cycles are differentiated from each other by at least a predetermined value by the time setting changers of the microwave sensors.

* * * * *